US009868673B2

(12) United States Patent
Furuya et al.

(10) Patent No.: US 9,868,673 B2
(45) Date of Patent: Jan. 16, 2018

(54) METHOD FOR MANUFACTURING MAGNESIUM FLUORIDE SINTERED COMPACT, METHOD FOR MANUFACTURING NEUTRON MODERATOR, AND NEUTRON MODERATOR

(71) Applicants: NIPPON LIGHT METAL COMPANY, LTD., Tokyo (JP); Cancer Intelligence Care Systems, Inc., Tokyo (JP); SINTER LAND Incorporation, Ltd., Niigata (JP)

(72) Inventors: Hidaka Furuya, Inazawa (JP); Kazuto Sanada, Tokyo (JP); Yoshinori Sugawara, Tokyo (JP); Hideaki Usui, Tokyo (JP); Masaru Nakamura, Tokyo (JP); Shinichi Takei, Niigata (JP)

(73) Assignees: NIPPON LIGHT METAL COMPANY, LTD., Tokyo (JP); CANCER INTELLIGENCE CARE SYSTEMS, INC., Tokyo (JP); SINTER LAND INCORPORATION, LTD., Niigata (JP)

( * ) Notice: Subject to any disclaimer, the term of this patent is extended or adjusted under 35 U.S.C. 154(b) by 0 days.

(21) Appl. No.: 15/216,536

(22) Filed: Jul. 21, 2016

(65) Prior Publication Data
US 2016/0326062 A1 Nov. 10, 2016

Related U.S. Application Data

(63) Continuation of application No. PCT/JP2015/051419, filed on Jan. 20, 2015.

(30) Foreign Application Priority Data

Jan. 22, 2014 (JP) .................................. 2014-009883

(51) Int. Cl.
G21F 1/02 (2006.01)
G21F 3/00 (2006.01)
(Continued)

(52) U.S. Cl.
CPC .............. *C04B 35/553* (2013.01); *A61N 5/10* (2013.01); *C04B 35/645* (2013.01);
(Continued)

(58) Field of Classification Search
USPC ......... 250/505.1, 506.1, 515.1, 516.1, 517.1, 250/518.1, 519.1
See application file for complete search history.

(56) References Cited

U.S. PATENT DOCUMENTS 3,301,781 A * 1/1967 Rice ...................... C04B 35/553
264/332
5,880,478 A 3/1999 Bishop et al.
(Continued)

FOREIGN PATENT DOCUMENTS

EP 1895819 3/2008
JP 7-216409 A 8/1995
(Continued)

OTHER PUBLICATIONS

O.E. Kononov et al., Optimization of an accelerator-based epithermal neutron source for neutron capture therapy, Applied Radiation and Isotopes 61 (Nov. 2004) p. 1009-1013.
(Continued)

*Primary Examiner* — Nicole Ippolito
(74) *Attorney, Agent, or Firm* — McDermott Will & Emery LLP

(57) ABSTRACT

There are provided a method for manufacturing a magnesium fluoride sintered compact to be free from cracks and chipping and to have high relative density, a method for manufacturing a neutron moderator, and the neutron mod-
(Continued)

erator. The method for manufacturing a magnesium fluoride sintered compact includes a powder filling process for filling a magnesium fluoride powder material into a die by tapping, and an intermediate body sintering (pulsed electric current sintering) process for performing pulsed electric current sintering for sintering the filled magnesium fluoride powder material while applying a pulsed electric current thereto, to obtain a magnesium fluoride sintered compact (intermediate body).

7 Claims, 10 Drawing Sheets

(51) Int. Cl.
| | |
|---|---|
| C04B 35/553 | (2006.01) |
| A61N 5/10 | (2006.01) |
| G21K 1/10 | (2006.01) |
| C04B 35/645 | (2006.01) |
| C04B 37/00 | (2006.01) |

(52) U.S. Cl.
CPC .............. *C04B 37/001* (2013.01); *G21K 1/10* (2013.01); *A61N 2005/109* (2013.01); *A61N 2005/1095* (2013.01); *C04B 2235/666* (2013.01); *C04B 2237/36* (2013.01)

(56) References Cited

U.S. PATENT DOCUMENTS

| | | | | |
|---|---|---|---|---|
| 2010/0248935 | A1* | 9/2010 | Teratani | B32B 18/00 501/119 |
| 2012/0211284 | A1* | 8/2012 | DiGiovanni | B22F 3/10 175/428 |
| 2016/0082282 | A1* | 3/2016 | Kumada | A61N 5/10 252/478 |
| 2016/0220839 | A1* | 8/2016 | Kuri | H05H 3/06 |

FOREIGN PATENT DOCUMENTS

| | | |
|---|---|---|
| JP | 11-139862 A | 5/1999 |
| JP | H11-228248 A | 8/1999 |
| JP | 2003-049207 A | 2/2003 |
| JP | 2004-233168 A | 8/2004 |
| JP | 2008-230904 | 10/2008 |
| JP | 2009-192488 A | 8/2009 |
| JP | 2013-217874 A | 10/2013 |
| RU | 2436877 C1 | 12/2011 |
| UA | 12384 A | 2/1997 |
| WO | 2014/010704 A1 | 1/2014 |

OTHER PUBLICATIONS

Reappraisal of the optimal neutron energy characteristic and spectrum for accelerator-based epithermal neutron source—PHITS analysis and trial production of the moderator, 15th International congress on Neutron Capture Therapy, Sep. 10-14, 2012.

Development of Accelerator Type Neutron Capture Therapy System Using New Material Target Technology for Recurrent Cancer Therapy, Feb. 2013 (CICS Co., Ltd.), http://www.med-device.jp/pdf/development/vp/H24-105)24.pdf.

O.E. Kononov et al., Accelerator-Based Source of Epithermal Neutrons for Neutron Capture Therapy, Atomic Energy, vol. 97, No. 3 (Sep. 2004), p. 626-631.

International Search Report PCT/JP2015/051419 dated Apr. 21, 2015 with English translation.

O. E. Kononov et al., "Accelerator-Based Source of Epithermal Neutrons for Neutron Capture Therapy", Atomic Energy, vol. 97, No. 3, 2004, pp. 626-631.

"Development of Accelerator Type Neutron Capture Therapy System Using New Material Target Technology for Recurrent Cancer Therapy", Report of Research Products (Summary Version), Feb. 2013, pp. 1-23 with English translation.

R. Inoue et al., "Optimum design of a moderator system based on dose calculation for an accelerator driven Boron Neutron Capture Therapy", Applied Radiation and Isotopes 83, (2014), pp. 225-228.

B. Khorsandi et al., "Optimizing the OSU-ABNS Base Moderator Assembly Materials for BNCT", Eleventh World Congress on Neutron Capture Therapy (ISNCT-11), 2004, pp. 1-10.

Youichi Shirakawa et al., "Preparation of MgF2 Sintered Body by Normal Sintering Combined with Capsule-Free Hot-Isostatic Pressing Treatment," Journal of the Ceramic Society of Japan, vol. 107, No. 12, pp. 1137-1139 (1999).

Extended European Search Report issued in corresponding European Patent Application No. 15740248.8, dated Aug. 30, 2017.

Notice of Reasons for Revocation of a Patent issued in JP Patent 6085782B dated Nov. 13, 2017.

Masao Tokita, "Recent and Future Progress on Advanced Ceramics Sintering by Spark Plasma Sintering (SPS) Mehod", Ceramics, vol. 49, No. 2, pp. 91-96 (Feb. 2014).

Written Opposition to the grant of JP Patent 6085782B, filed Jun. 6, 2017.

Office Action issued in Russian Patent Application No. 2016133616, dated Oct. 23, 2017.

E.N. Poddenezhnyi et al., "Ceramic Fluoride Targets for Magnetron Sputtering Formed by a Method of Semidry Compaction with Vacuum Sealing", VESTNIK of GSTU named after P.O.SUKHOI, No. 3, pp.62-67 (2012). (w/English Abstract).

\* cited by examiner

METHOD FOR MANUFACTURING MAGNESIUM FLUORIDE SINTERED COMPACT, METHOD FOR MANUFACTURING NEUTRON MODERATOR, AND NEUTRON MODERATOR

CROSS-REFERENCE TO RELATED APPLICATIONS

This application is a continuation of International Application No. PCT/JP2015/051419, filed on Jan. 20, 2015, which claims priority to Japanese Application No. 2014-009883, filed on Jan. 22, 2014. The contents of these applications are incorporated herein by reference in their entirety.

BACKGROUND

1. Technical Field

The present invention relates to a neutron moderator mainly used for neutron capture therapy, a method for manufacturing the neutron moderator, and a method for manufacturing a magnesium fluoride sintered compact that is optimal for a neutron moderator.

2. Description of the Related Art

Various materials have been studied for a neutron moderator that is used for selective treatment of cancer such as boron neutron capture therapy. Examples of the materials include lithium fluoride, aluminum fluoride, and magnesium fluoride. Of these materials, magnesium fluoride is specifically known as an optimal material for a neutron moderator due to its excellent function in moderating the energy of neutron beams to 10 key or lower.

The technique described in Japanese Patent Application Laid-open No. 2004-233168 (JP-A-2004-233168) mentioned above uses lithium fluoride for a neutron moderator. Lithium used in the technique described in JP-A-2004-233168, however, presents an issue of manufacturing cost, because Lithium is one of rare metals.

In view of the above issue, "Optimizing the OSU-ABNS Base Moderator Assembly Materials for BNCT B. Khorsandia*, T. E. Blue a Nuclear Engineering Program, The Ohio State University, Columbus, Ohio 43210, USA" describes that magnesium fluoride has an excellent neutron moderating function for moderating the energy of neutrons in the range of 10 keV or lower. In addition, "Accelerator-Based source of epithermal neutrons for neutron capture therapy. Kononov O E, Kononov V N, Solov' EV A N, Bokhovko M V At Energy Vol. 97 No. 3, PP 626-631" describes a moderator combining magnesium fluoride and polytetrafluoroethylene.

In order to manufacture a neutron moderator only with magnesium fluoride and without using polytetrafluoroethylene to have a good neutron moderating performance, it is appropriate to process magnesium fluoride into a sintered compact. For a neutron moderator, a magnesium fluoride sintered compact is preferably made into a predetermined size, to be free from cracks and chipping and to have high relative density.

The present invention has been made in view of the above considerations, and is directed to providing a method for manufacturing a magnesium fluoride sintered compact to be free from cracks and chipping and to have high relative density, and also providing a method for manufacturing a neutron moderator, and the neutron moderator.

SUMMARY

According to an aspect of the present invention in order to solve the above-mentioned problems and achieve the purpose, a method for manufacturing a magnesium fluoride sintered compact is provided. The method includes: filling a magnesium fluoride powder material into a die by tapping; and performing pulsed electric current sintering for sintering the filled magnesium fluoride powder material while applying a pulsed electric current thereto, to obtain a magnesium fluoride sintered compact.

This manufacturing method provides a sintered compact having less variation in grain size distribution and having suppressed grain size growth, and hence enabling the sintered compact to be free from cracks and chipping and to have high relative density.

According to a preferred aspect, it is preferable that in the powder filling, the magnesium fluoride powder material is a high-purity material having a purity of 99 percent by mass or higher, and the rest thereof contains inevitable impurities. The magnesium fluoride sintered compact made of such a high-purity material can suppress neutrons having energy of lower than 0.5 eV. In addition, the magnesium fluoride sintered compact can also suppress neutrons having energy of higher than 10 keV.

In order to solve the above-mentioned problems and achieve the purpose, a method for manufacturing a neutron moderator is provided. The method includes: preparing a plurality of disc-shaped magnesium fluoride sintered compacts manufactured by the above-mentioned method for manufacturing a magnesium fluoride sintered compact; and layering and joining the disc-shaped magnesium fluoride sintered compacts to manufacture a neutron moderator. This manufacturing method eliminates the necessity of sintering a single thick large magnesium fluoride sintered compact, and prevents relative density inside the neutron moderator from becoming low.

According to a preferred aspect, when the disc-shaped magnesium fluoride sintered compacts are used as intermediate bodies, it is preferable that in the layering and joining, at least one second intermediate layered body is layered, the second intermediate layered body being obtained by further drilling the intermediate bodies. This manufacturing method enables precise drilling of disc-shaped magnesium fluoride sintered compacts that have low processabiltiy.

According to a preferred aspect, it is preferable that in the layering and joining, when the disc-shaped magnesium fluoride sintered compacts are used as intermediate bodies, at least one third intermediate layered body is layered, the third intermediate layered body being obtained by tapering an outer periphery of the intermediate bodies. This manufacturing method enables precise tapering of magnesium fluoride sintered compacts that are prone cracking or chipping on their outer peripheries by processing the magnesium fluoride sintered compacts in a disc shape.

According to a preferred aspect, it is preferable that in the layering and joining, a neutron moderator is manufactured by layering a first intermediate layered body in which the intermediate bodies are layered, the second intermediate layered body, and the third intermediate layered body. This process can provide a neutron moderator containing magnesium fluoride sintered compacts to be free from cracks and chipping and to have high relative density.

In order to solve the above-mentioned problems and achieve the purpose, a neutron moderator that moderates neutrons is provided, the neutron moderator including an intermediate layered body in which a plurality of disc-shaped magnesium fluoride sintered compacts are layered.

The neutron moderator can suppress neutrons having an energy of lower than 0.5 eV by the magnesium fluoride sintered compacts to be free from cracks and chipping and to have high relative density. The neutron moderator can also suppress neutrons having energy of higher than 10 key by the magnesium fluoride sintered compacts to be free from cracks and chipping and to have high relative density.

The present invention provides a method for manufacturing a magnesium fluoride sintered compact to be free from cracks and chipping and to have high relative density, a method for manufacturing a neutron moderator, and the neutron moderator.

DETAILED DESCRIPTION

The following describes an embodiment for carrying out the present invention in detail with reference to the accompanied drawings. The description in the following embodiment is not intended to limit the present invention. Components described below include those that can easily be conceived by those skilled in the art and that are substantially the same. Furthermore, the components described below can be combined as appropriate.

(Neutron Source Generator)

Figure 1:
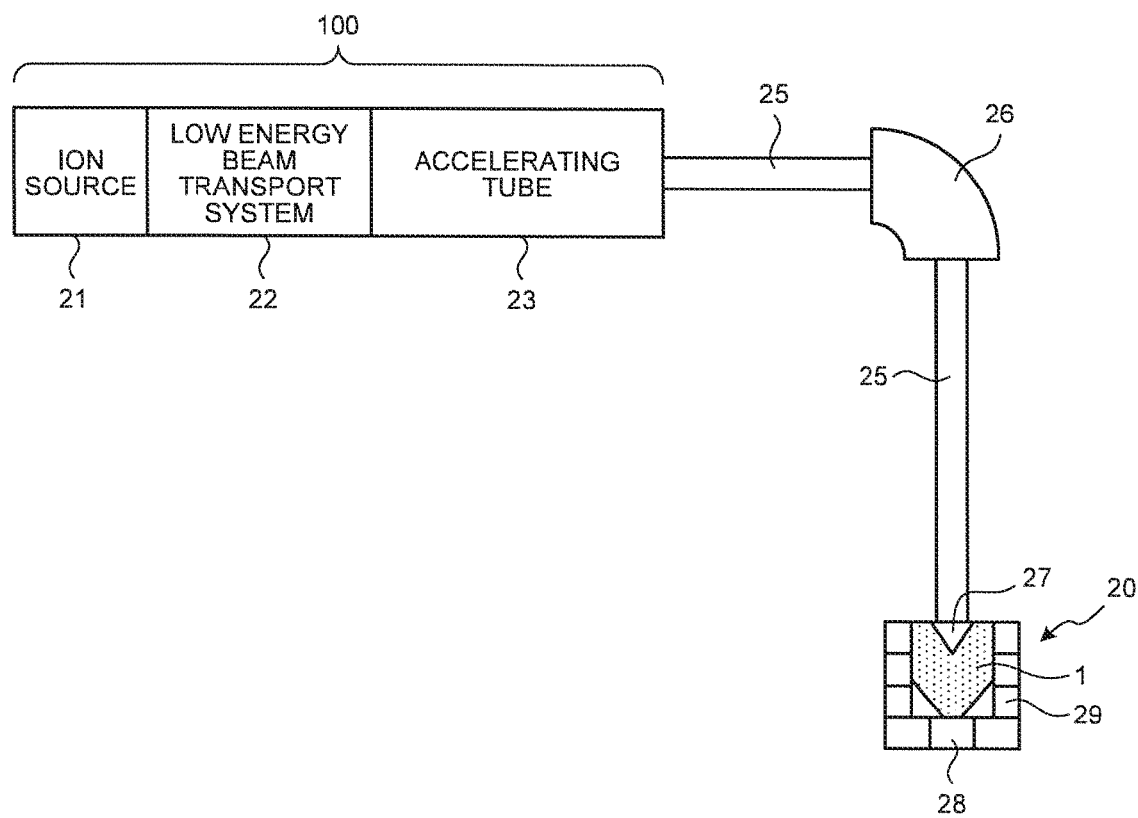
FIG. 1 is a diagram for explaining a neutron source generator including a neutron moderator according to an embodiment of the present invention.

FIG. 1 is a diagram for explaining a neutron source generator including a neutron moderator according to an embodiment of the present invention. As illustrated in FIG. 1, the neutron source generator includes an accelerator 100, a beam transport 25, a bending magnet 26, and a target unit 20.

The accelerator 100 is a device for accelerating protons and is provided with an ion source 21, a low energy beam transport system (LEBT) 22, and an accelerating tube 23 in this order from upstream to downstream. The ion source 21 is a device for turning protons into cations. The low energy beam transport system 22 is an interface between the ion source 21 and the accelerating tube 23.

The beam transport 25 is a beam passage for guiding protons accelerated by the accelerator 100 to the target unit 20. The beam transport 25 changes the traveling direction of the accelerated protons through the bending magnet 26 so that the protons are guided to the target unit 20 disposed in an optional position. As described above, the bending magnet 26 is used to bend the traveling direction of the protons accelerated by the accelerator 100. The beam transport 25 may guide the protons accelerated by the accelerator 100 to the target unit 20 without using the bending magnet 26.

The target unit 20 is a device for generating neutrons by a reaction of protons and a target 27. The target unit 20 includes the target 27, a neutron moderator 1, a neutron reflector 29, and an irradiation part 28.

The target 27 includes a base (substrate), such as of copper, on which a target material, such as a thin film of metallic lithium, is deposited. The target 27 described in the embodiment is a cone-shaped target with a lithium thin film provided on its inner wall surface (inner surface). The target is not limited to this shape. A target of any shape, for example, a plate-shaped target with a lithium thin film provided on its surface, may be used. The target material may be another target material such as beryllium. The neutron moderator 1 moderates neutrons generated by the target 27.

The neutron reflector 29 is made of lead, for example, and surrounds the target 27 and the neutron moderator 1 to prevent unnecessary release of neutrons to the outside of the target unit 20. The irradiation part 28 is an opening for releasing the neutrons moderated by the neutron moderator 1.

Neutron capture therapy, which selectively kills cancer cells, has been studied recently and clinically tested in nuclear facilities. The neutron source generator illustrated in FIG. 1 can provide neutrons without use of a nuclear reactor. In neutron capture therapy, medicine is prepared from a chemical compound containing a substance, such as non-radioactive isotope boron-10 (5-10) that easily causes nuclear reaction with thermal neutrons, for example. The medicine is preliminarily administered to a human so that the medicine is absorbed in an area where cancer exists, i.e., only in cancer cells coexisting with normal cells. Neutron capture therapy is cancer therapy to selectively suppress only cancer cells by irradiating, by the neutron source generator illustrated in FIG. 1, a cancer site with neutrons (thermal neutrons and epithermal neutrons) of an energy that has less influence on a human body.

The neutron moderator 1 needs to moderate the energy of the released neutrons to the range of 10 keV or lower so that the neutrons (thermal neutrons and epithermal neutrons)

have an energy that has less influence on a human body. The neutron moderator 1 of the embodiment is made from magnesium fluoride and moderates neutrons, and thus presents high neutron moderating performance in the energy range of 20 keV or lower.

Effective neutron energy used as radiation for treating recurrent cancer is generally from 0.5 eV to 10 keV, Neutron energy of lower than 0.5 eV is likely to affect normal tissues in a skin surface of a human body, while neutron energy of higher than 10 keV has a larger effect on normal tissues other than cancer tissues inside a human body. Compared to a heavy water moderator, the neutron moderator 1 of the embodiment can suppress more neutrons having energy of lower than 0.5 eV than the heavy water moderator does. Compared to a polytetrafluoroethylene moderator, the neutron moderator 1 of the embodiment can suppress more neutrons having energy of higher than 10 keV than the polytetrafluoroethylene moderator does.

In order for the neutron moderator 1 of the embodiment made of magnesium fluoride to have a predetermined passage cross-sectional area, it is preferable that magnesium fluoride be formed into a sintered compact. However, if a magnesium fluoride sintered compact has enough size as the neutron moderator 1 of the embodiment, it has been found that a magnesium fluoride sintered compact needs some technique to maintain the quality of its sintered state, such as preventing cracking or chipping. The following describes the neutron moderator 1 in detail with reference to FIG. 2 to FIG. 17.

(Neutron Moderator)

Figure 2:
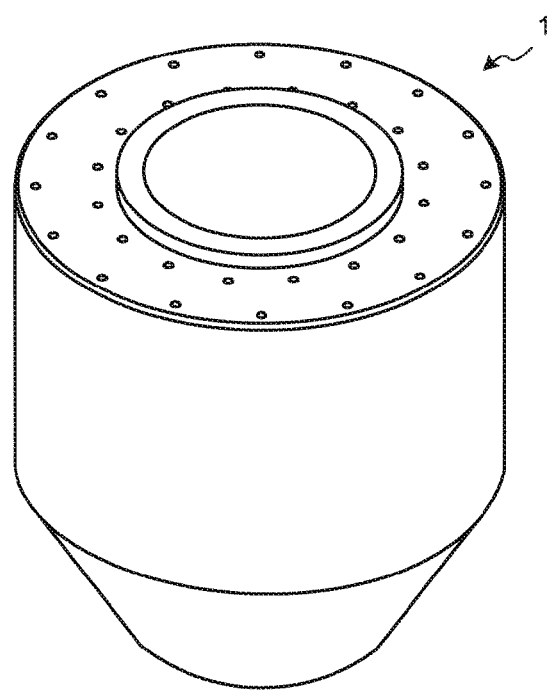
FIG. 2 is a perspective view of the neutron moderator according to the embodiment.
Figure 3:
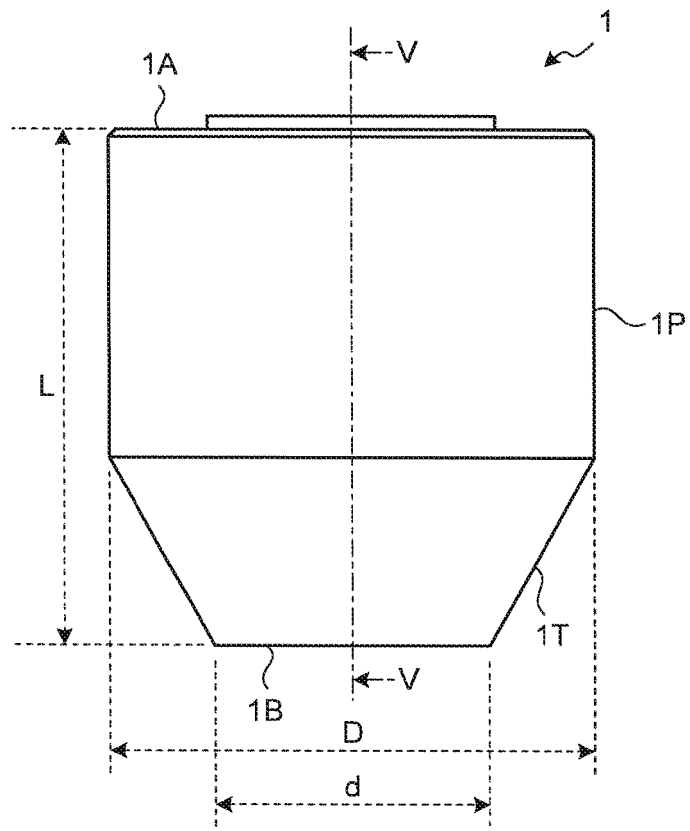
FIG. 3 is a side view of the neutron moderator in FIG. 2.
Figure 4:
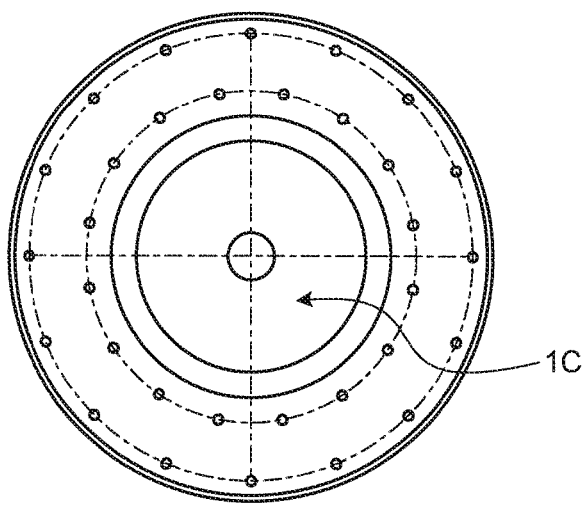
FIG. 4 is a top view of the neutron moderator in FIG. 2.
Figure 5:
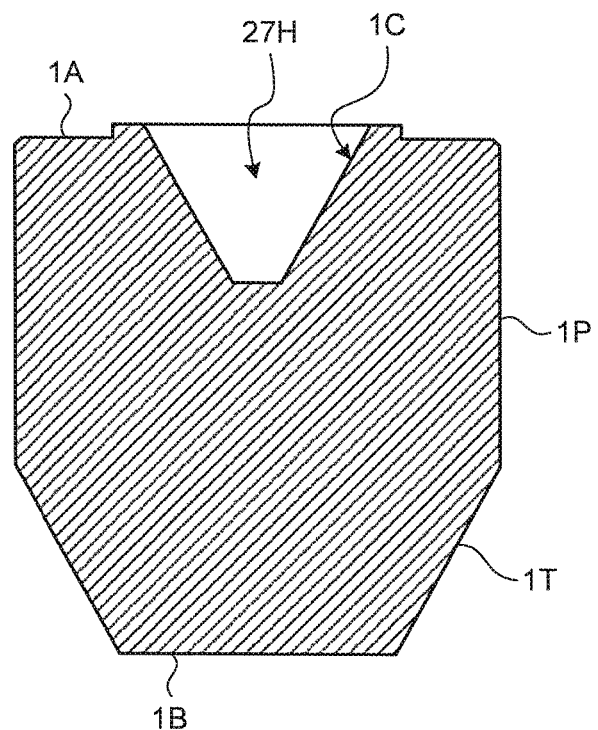
FIG. 5 is a cross sectional view taken along line V-V in FIG. 3.

FIG. 2 is a perspective view of the neutron moderator according to the embodiment. FIG. 3 is a side view of the neutron moderator in FIG. 2. FIG. 4 is a top view of the neutron moderator in FIG. 3. FIG. 5 is a cross sectional view taken along line V-V in FIG. 3. The neutron moderator 1, as illustrated in FIG. 3, is a substantially cylindrical body having a top surface 1A on the target 27 side illustrated in FIG. 1, a bottom surface 1B on the irradiation part 28 side illustrated in FIG. 1, and an outer periphery 1P. As illustrated in FIG. 3, assuming that the thickness of the neutron moderator 1 is a thickness L in the travelling direction of neutrons from the target 27 to the irradiation part 28 illustrated in FIG. 1, the neutral moderator 1 tends to have a ratio of the thickness L to a diameter D (thickness L/diameter D) being 180% or larger. When the neutron moderator 1 in such a shape is sintered as one piece, the inside of the neutron moderator 1 may have lower relative density due to non-uniform pressurization. The non-uniform relative density of the neutron moderator 1 may affect the moderation of neutrons. The neutron moderator 1 may develop cracks or chips on its outer periphery portion when the size of the neutron moderator 1 is large (specifically, with a diameter (φ) of 150 mm or larger).

As illustrated in FIG. 4 and FIG. 5, the top surface 1A of the neutron moderator 1 has a tapered surface 1C of a depressed part 27H into which the target 27 illustrated in FIG. 1 is inserted. As illustrated in FIG. 3, the neutron moderator 1 has an outer peripheral tapered surface 1T, the diameter of which decreases toward the bottom surface 1B, so that a diameter d of the bottom surface 1B is smaller than the diameter D of the outer periphery 1P. If the tapered surface 1C and the tapered surface 1T have large areas, it is difficult to manufacture the neutron moderator 1 with a high precision shape.

In view of the above, the inventors studied a method for manufacturing a magnesium fluoride sintered compact having a high yield and less cracks by applying a solid compression sintering method called spark plasma sintering (SPS) or pulsed electric current sintering, and thus developed the embodiment.

Figure 6:
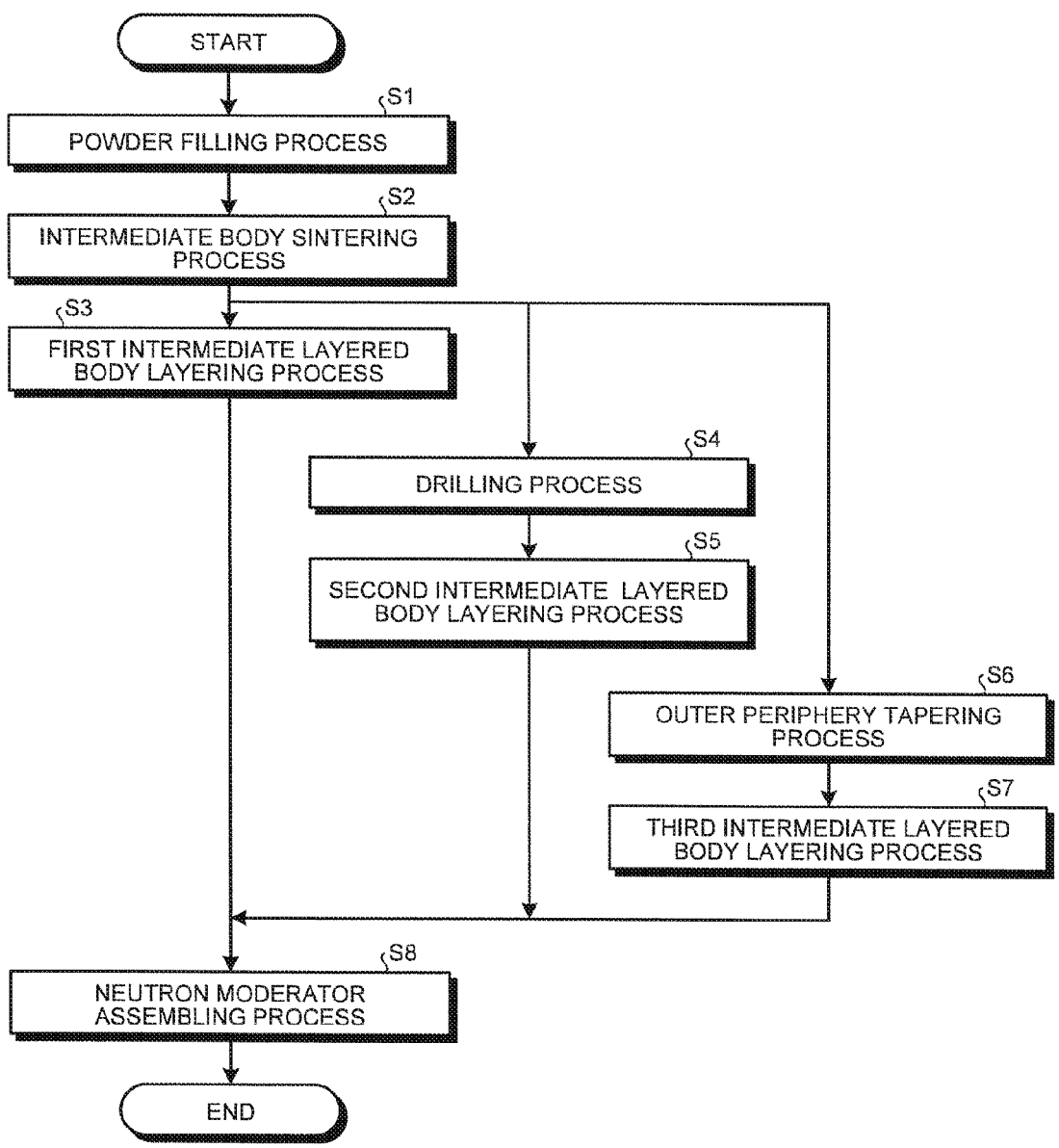
FIG. 6 is a flowchart for explaining a method for manufacturing the neutron moderator according to the embodiment.
Figure 7:
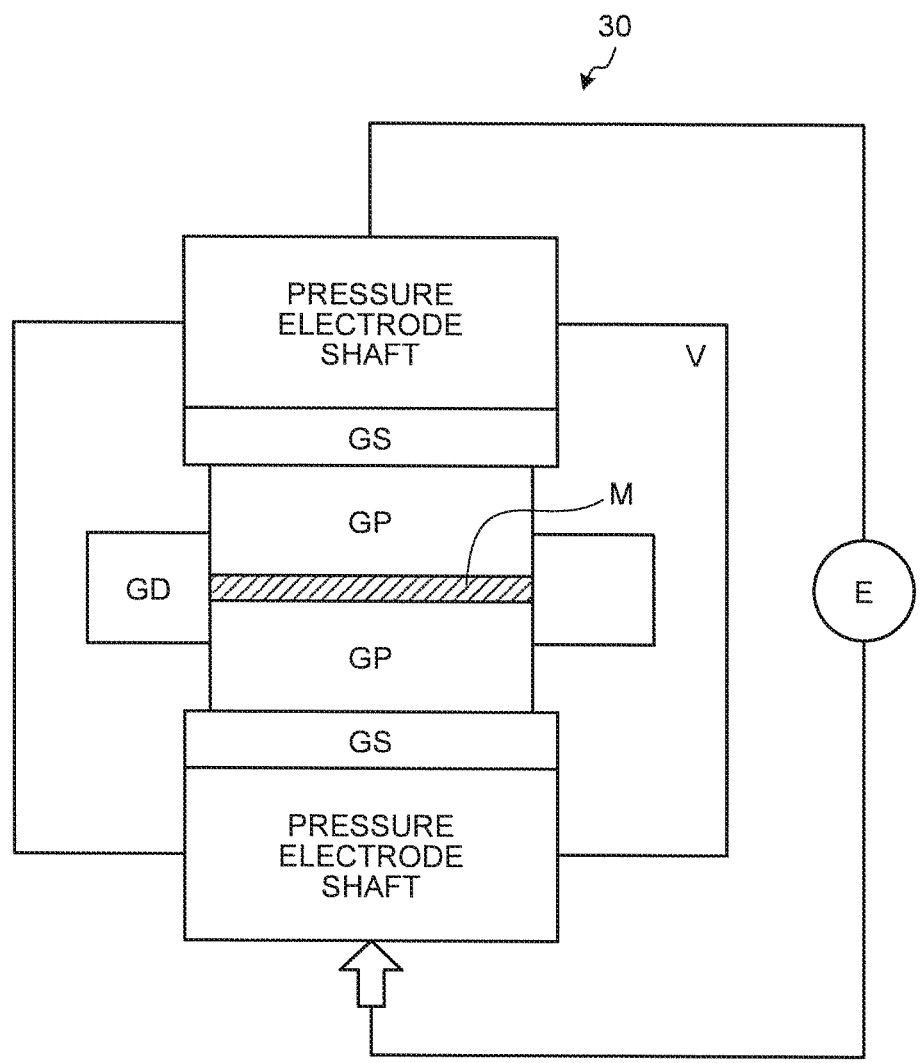
FIG. 7 is a schematic diagram schematically illustrating a pulsed electric current sintering device.

FIG. 6 is a flowchart for explaining a method for manufacturing the neutron moderator according to the embodiment. FIG. 7 is a schematic diagram illustrating a pulsed electric current sintering device. As illustrated in FIG. 6, a method for manufacturing a sintered compact according to the embodiment includes a powder filling process S1 and an intermediate body sintering process S2. The method for manufacturing the neutron moderator according to the embodiment, further includes in a layering process, a first intermediate layered body layering process S3, a drilling process S4, a second intermediate layered body layering process S5, an outer periphery tapering process S6, a third intermediate layered body layering process S7, and a neutron moderator assembling process S8.

As illustrated in FIG. 7, a spark plasma sintering device 30 includes a chamber V the inside atmosphere of which can be vacuum or purged with Argon or Nitrogen gas, a graphite die GD, graphite punches GP, graphite spacers GS, pressure electrode shafts, and a direct current pulse power source E. The graphite die GD, the graphite punches GP, the graphite spacers GS, and the pressure electrode shafts are made of a conductive material such as stainless steel.

The direct current pulse power source E can apply ON-OFF direct current pulse to a magnesium fluoride powder M in the graphite die GD through the graphite die GD, the graphite punches GP, and the pressure electrode shafts.

In the method for manufacturing the sintered compact according to the embodiment, at the powder filling process S1, magnesium fluoride powder is prepared and filled by tapping.

Figure 8:
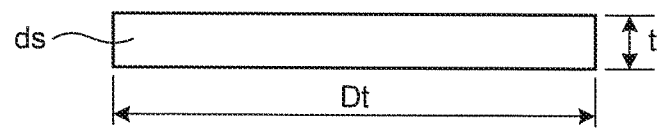
FIG. 8 is a side view of a disc-shaped magnesium fluoride sintered compact according to the embodiment.
Figure 9:
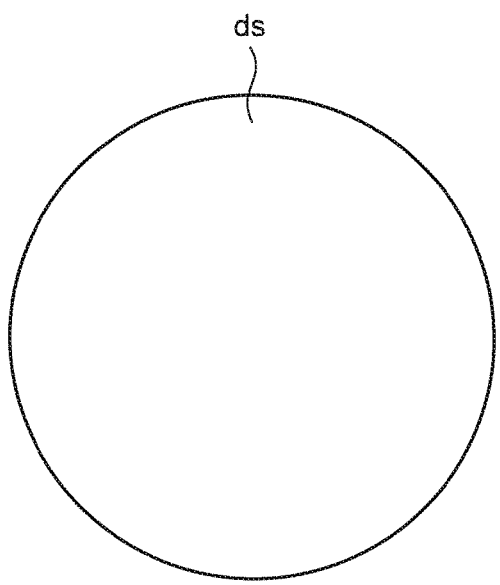
FIG. 9 is a top view of the magnesium fluoride sintered compact in FIG. 8.

In the method for manufacturing the sintered compact according to the embodiment, at the intermediate body sintering process S2, pulsed electric current sintering is performed for sintering while applying a pulsed electric current. The magnesium fluoride powder in the graphite die GD is compressed into a disc shape with pressure P applied by the graphite punches GP and the pressure electrode shafts. FIG. 8 is a side view of a disc-shaped magnesium fluoride sintered compact according to the embodiment. FIG. 9 is a top view of the magnesium fluoride sintered compact in FIG. 8. A magnesium fluoride sintered compact ds according to the embodiment is, for example, a disc (flat cylindrical body) having a thickness t and a diameter Dt. The ratio of the thickness t to the diameter Dt preferably from 8% to 15%. This configuration can prevent the disc-shaped magnesium fluoride sintered compact ds from being cracked or chipped.

Subsequently in the method for manufacturing the neutron moderator according to the embodiment, at the first intermediate layered body layering process S3, a plurality of disc-shaped magnesium fluoride sintered compacts ds are manufactured and prepared as intermediate bodies, and then layered and joined together along their thickness at the first intermediate layered body layering process S3.

Figure 10:
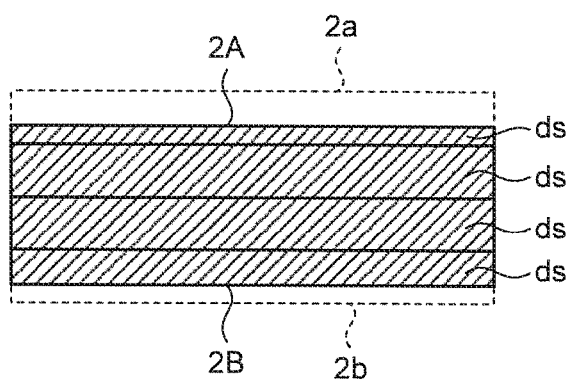
FIG. 10 is a diagram for explaining a layered state of intermediate bodies of a first intermediate layered body according to the embodiment.
Figure 11:
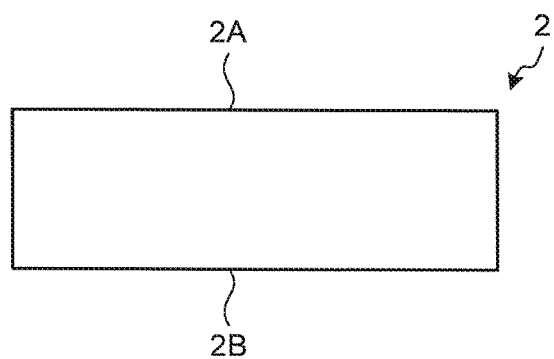
FIG. 11 is a schematic diagram illustrating the first intermediate layered body according to the embodiment.

FIG. 10 is a diagram for explaining a layered state of intermediate bodies of a first intermediate layered body according to the embodiment. FIG. 11 is a schematic diagram illustrating the first intermediate layered body according to the embodiment. As illustrated in FIG. 10, all of the disc-shaped magnesium fluoride sintered compacts ds do not necessarily have the same thickness. For example, a surface 2a of one of the disc-shaped magnesium fluoride sintered compacts ds arranged on the top may be scraped off so that a top surface 2A is exposed. In addition, a surface 2b of one of the disc-shaped magnesium fluoride sintered compacts ds arranged on the bottom may be scraped off so that a bottom surface 2B is exposed. Thereafter, in the method for manufacturing the neutron moderator according to the embodiment, a first intermediate layered body 2 illustrated in FIG. 11 is manufactured in the layering process. The first intermediate layered body has a cylindrical shape.

Figure 12:
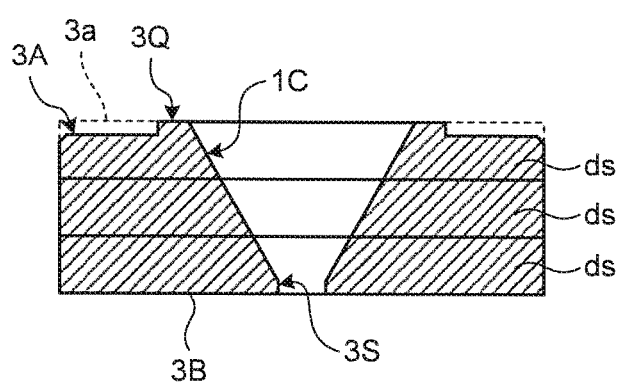
FIG. 12 is a diagram for explaining a layered state of intermediate bodies of a second intermediate layered body according to the embodiment.
Figure 13:
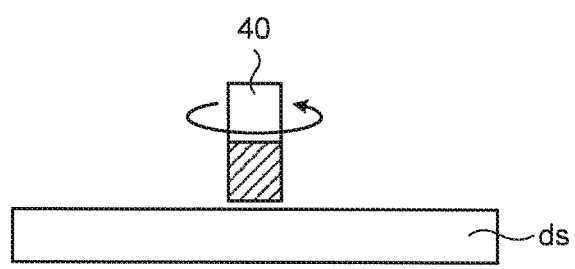
FIG. 13 is a diagram for explaining a machining process for manufacturing the second intermediate layered body according to the embodiment.
Figure 14:
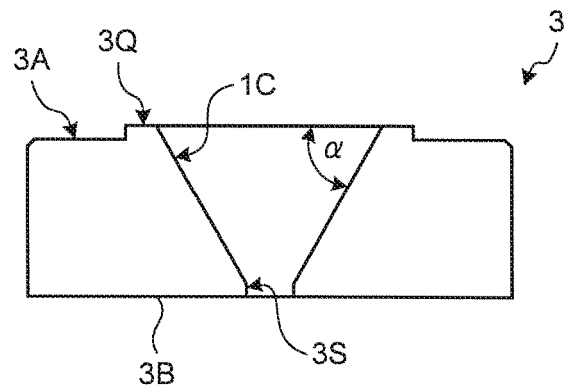
FIG. 14 is a schematic diagram illustrating the second intermediate layered body according to the embodiment.

Subsequently in the method for manufacturing the neutron moderator according to the embodiment, at the drilling process 54 in the layering process, a plurality of disc-shaped magnesium fluoride sintered compacts ds are drilled in the center portions on their top surfaces. FIG. 12 is a diagram for explaining a layered state of intermediate bodies of a second intermediate layered body according to the embodiment. FIG. 13 is a diagram for explaining a machining process for manufacturing the second intermediate layered body according to the embodiment. FIG. 14 is a schematic diagram illustrating the second intermediate layered body according to the embodiment.

In the embodiment, the tapered surface 10 needs to be made smooth as illustrated in FIG. 12. As illustrated in FIG. 13, in the machining process of the embodiment, one of the disc-shaped magnesium fluoride sintered compacts ds is drilled to form the tapered surface 1C with a drill 40 that is rotated while being revolved spirally. When the magnesium fluoride sintered compact ds is drilled from one surface, cracking or chipping tends to occur immediately before the drill 40 penetrates the other surface. For this reason, it is preferable that the spiral revolution of the drill 40 of a cutting device should be stopped immediately before the drill 40 penetrates the other surface of the magnesium fluoride sintered compact ds, and the drill 40 moves linearly along the thickness direction. By doing so and as illustrated in FIG. 12, it is possible to form a vertical inner wall 35 that extends in a vertical direction through the tapered surface 1C and a bottom surface 35 of a disc-shaped magnesium fluoride sintered compact ds, and thus this process secures the thickness of a finally processed portion of the tapered surface 1C, which prevents cracking and chipping.

Subsequently in the method for manufacturing the neutron moderator according to the embodiment, in the layering process, the disc-shaped magnesium fluoride sintered compacts ds that have been drilled at the drilling process S4 are manufactured and prepared as intermediate bodies, and then layered and joined together along the thickness direction at the second intermediate layered body layering process S5.

As illustrated in FIG. 12, all of the disc-shaped magnesium fluoride sintered compacts ds do not necessarily have the same thickness. For example, a surface 3a of one of the disc-shaped magnesium fluoride sintered compacts ds arranged on the top may be scraped off so that a top surface 3A is exposed while a protrusion 3Q remains around an edge of the tapered surface 1C. As described above, in the method for manufacturing the neutron moderator according to the embodiment, a second intermediate layered body 3 illustrated in FIG. 14 is manufactured in the layering process. The second intermediate layered body 3 has a cylindrical outer shape. An angle α of the tapered surface 1C is preferably a constant angle while considering the order of the disc-shaped magnesium fluoride compacts ds to be layered.

Figure 15:
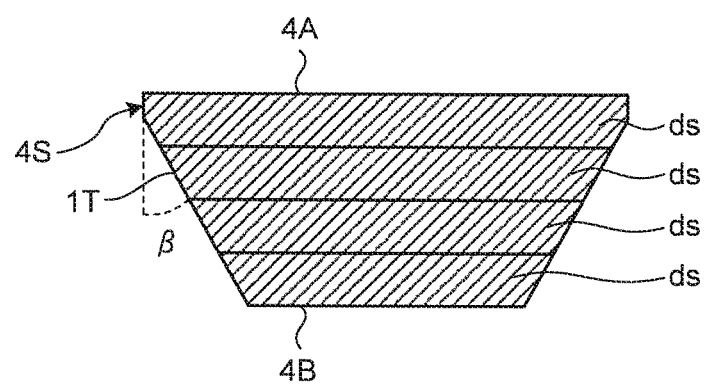
FIG. 15 is a diagram for explaining a layered state of intermediate bodies of a third intermediate layered body according to the embodiment.
Figure 16:
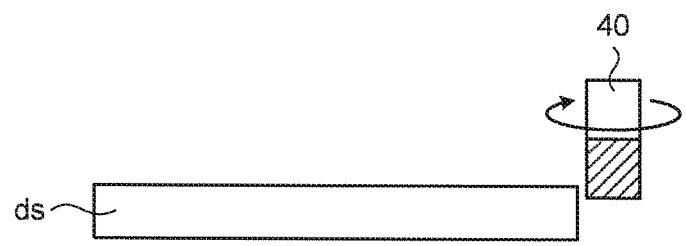
FIG. 16 is a diagram for explaining a machining process for manufacturing the third intermediate layered body according to the embodiment.
Figure 17:
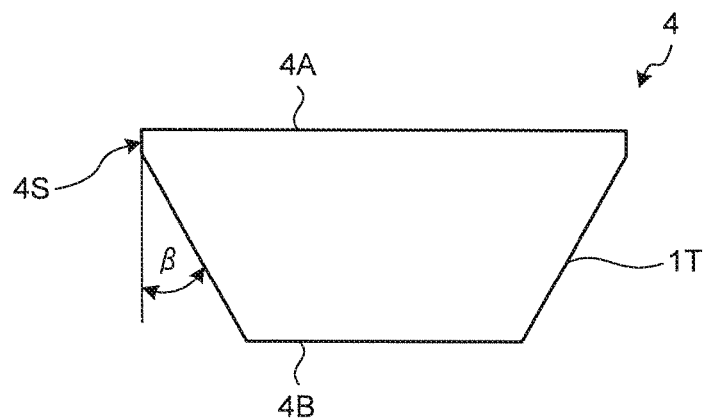
FIG. 17 is a schematic diagram illustrating the third intermediate layered body according to the embodiment.

Subsequently in the method for manufacturing the neutron moderator according to the embodiment, at the outer periphery tapering process S6, a plurality of disc-shaped magnesium fluoride sintered compacts ds are tapered on their outer periphery portions. FIG. 15 is a diagram for explaining a layered state of intermediate bodies of a third intermediate layered body according to the embodiment. FIG. 16 is a diagram for explaining a machining process for manufacturing the third intermediate layered body according to the embodiment. FIG. 17 is a schematic diagram illustrating the third intermediate layered body according to the embodiment.

In the embodiment, the tapered surface 1T needs to be made smooth as illustrated in FIG. 15. As illustrated in FIG. 16, at the machining process of the embodiment, one of the disc-shaped magnesium fluoride sintered compacts ds is machined to form the tapered surface 1T with the drill 40 being pressed against the disc-shaped magnesium fluoride sintered compact ds from its outer periphery. The magnesium fluoride sintered compact ds may have a cylindrical portion 4S left as illustrated in FIG. 15. An angle β of the tapered surface 1T is preferably a constant angle while considering the order of the disc-shaped magnesium fluoride compacts ds to be layered.

Subsequently in the method for manufacturing the neutron moderator according to the embodiment, in the layering process, the disc-shaped magnesium fluoride sintered compacts ds that have been tapered on their outer peripheries at the outer periphery tapering process S6 are manufactured and prepared as intermediate bodies, and then layered and joined together along the thickness direction at the third intermediate layered body layering process S7.

In the method for manufacturing the neutron moderator according to the embodiment, a third intermediate layered body 4 illustrated in FIG. 17 is manufactured in the layering process. The third intermediate layered body 4 has a substantially truncated conical outer shape having a top surface 4A, a bottom surface 4B, and the tapered surface 1T.

Thereafter, in the method for manufacturing the neutron moderator according to the embodiment, the top surface 2A of the first intermediate layered body 2 and the bottom surface 35 of the second intermediate layered body are joined together at the neutron moderator assembling process S8. The top surface 3A of the second intermediate layered body 3 becomes the top surface 1A of the neutron moderator. In addition, the bottom surface 25 of the first intermediate layered body 2 and the top surface 4A of the third intermediate layered body 4 are joined together. The bottom surface 4B of the third intermediate layered body 4 becomes the bottom surface 1B of the neutron moderator. The neutron moderator 1 is manufactured by layering the first intermediate layered body 2, the second intermediate layered body 3, and the third intermediate layered body 4.

As described above, the method for manufacturing a magnesium fluoride sintered compact includes the powder filling process S1 for filling a magnesium fluoride powder material into a die by tapping, and the intermediate body sintering (pulsed electric current sintering) process S2 for performing pulsed electric current sintering for sintering the filled magnesium fluoride powder material while applying a pulsed electric current thereto, to obtain a magnesium fluoride sintered compact (intermediate body). This manufacturing method provides a magnesium fluoride sintered compact ds having less variation in grain size distribution and suppressed grain growth, preventing cracking and chipping while increasing relative density.

The magnesium fluoride powder material filled at the powder filling process S1 is a high-purity material having a purity of 99 percent by mass or higher, but may contain inevitable impurities. A magnesium fluoride sintered compact ds made of such a material can suppress neutrons having energy of lower than 0.5 eV. In addition, the magnesium fluoride sintered compact ds can suppress neutrons having energy of higher than 10 keV.

The method for manufacturing a neutron moderator includes a preparation process for preparing disc-shaped magnesium fluoride sintered compacts ds manufactured by the method for manufacturing a magnesium fluoride sintered compact described above, and the layering process for layering and joining the disc-shaped magnesium fluoride sintered compacts ds to manufacture the neutron moderator 1. This method eliminates the necessity of sintering a thick large magnesium fluoride sintered compact ds, and hence can lower the possibility of decreasing the relative density inside the neutron moderator 1.

When the neutron moderator 1 includes the first intermediate layered body 2 in which disc-shaped magnesium fluoride sintered compacts ds are layered, the neutron moderator 1 also includes the second intermediate layered body 3 containing at least one intermediate body obtained at the machining process by drilling a magnesium fluoride sintered compact ds. By this manufacturing method, disc-shaped magnesium fluoride sintered compacts ds with low processabiltiy can be made thin, thereby it becomes easy to penetrate precisely holes of respective magnesium fluoride sintered compacts ds.

In case the neutron moderator 1 includes the first intermediate layered body 2 in which disc-shaped magnesium fluoride sintered compacts ds are layered, the neutron moderator 1 also includes the third intermediate layered body 4 containing at least one intermediate body obtained at the machining process by tapering the outer periphery of a magnesium fluoride sintered compact ds. By this manufacturing method, disc-shaped magnesium fluoride sintered compacts ds are made thin, improving the precision in processing the magnesium fluoride sintered compacts ds that are prone to cracking or chipping on their outer peripheries.

The neutron moderator 1 includes the first intermediate layered body 2 in which a plurality of disc-shaped magnesium fluoride sintered compacts ds are layered. The neutron moderator 1 can suppress neutrons having energy of lower than 0.5 eV by using the magnesium fluoride sintered compacts ds to be free from cracks and chipping and to have high relative density. The neutron moderator 1 can also suppress neutrons having energy of higher than 10 keV by using the magnesium fluoride sintered compacts ds to be free from cracks and chipping and to have high relative density.

The neutron moderator 1 contains the first intermediate layered body 2, the second intermediate layered body 3, and the third intermediate layered body 4 being layered, and thus presents a uniform performance for moderating neutrons at any one of the first intermediate layered body 2, the second intermediate layered body 3, and the third intermediate layered body 4.

EXAMPLES

To obtain samples, a magnesium fluoride powder (manufactured by Morita Chemical Industries Co., Ltd.) having a purity of 99% or higher was filled in a die vessel having an inner volume of a diameter φ (mm)×thickness (mm), and then powder filling was performed by tapping.

Subsequently, the vessel filled with the magnesium fluoride powder was set in a spark plasma sintering device, and a vacuum atmosphere was created as a sintering atmosphere by decompression. Cracking was checked under constant and variable pressurizing conditions. Examples and comparative examples were tested under the same electric current conditions of supplying a pulsed electric current having the maximum current output of approximately 18,000 A. The magnesium fluoride powder was heated at a heating rate ranging from 1° C./min to 15° C./min until it reached a holding temperature ranging from 630° C. to 900° C. A holding time was set to a value ranging from 15 minutes to 240 minutes. After cracking was checked, samples free from cracks were taken as examples while samples with cracks were taken as comparative examples.

According to the findings from the examples, the heating rate is preferably in the range of 1° C./min to 7° C./min. If the heating rate of the die is higher than 7° C./min, a temperature difference between the inside and the outside of the magnesium fluoride sintered compact becomes large, leading to problems of large difference in grain sizes, and to cracking problems. On the other hand, if the heating rate is 7° C./min or lower, it is possible to heat the magnesium fluoride sintered compact without causing such large difference in grains sizes. As a result, cracking of the sintered compact can be prevented. However, if the temperature increase rate is lower than 1° C./min, heating takes longer time, which causes a manufacturing efficiency problem.

According to the findings from the examples, the magnesium fluoride powder is not limited to a specific powder as long as it has high purity and concentration of 99.0% or higher. A general magnesium fluoride powder may be used, such as a powder obtained by, for example, adding hydrofluoric acid to a cation exchange resin, one of the cation exchange groups of which is generally magnesium, and then extracting and powdering the produced magnesium fluoride particles.

According to the findings from the examples, the pressurizing condition for the method for manufacturing the magnesium fluoride sintered compact is preferably about 20 MPa. If the pressurizing condition is lower than 20 MPa, the magnesium fluoride powder is not sufficiently compressed and large gaps are left among powder particles, which may cause cracking in the magnesium fluoride sintered compact. If the pressurizing condition is higher than 20 MPa, the outer periphery of the magnesium fluoride sintered compact may be prone to damage. If the pressurizing condition is higher than 20 MPa, there is a problem in the specification of a manufacturing device in that application of a high pressure on a large-sized magnesium fluoride sintered compact is difficult in light of the device's performance. Sintering is preferably performed under the constant pressurizing condition because the crystalline structure of a sintered compact is easy to be uniform.

According to the findings from the examples, the holding temperature for the method for manufacturing the magnesium fluoride sintered compact is preferably from 650 to 800° C. A holding temperature of lower than 650° C. requires a longer holding time to obtain uniform crystal grains, while a holding temperature of higher than 800° C. is not cost-effective, because the effect is saturated.

According to the findings from the examples, the holding time of die heating for the method for manufacturing the magnesium fluoride sintered compact is preferably 45 minutes or longer. A holding time of longer than 180 minutes may increase manufacturing cost, because the effect is saturated.

According to the findings from the examples, 99% or higher relative density can be achieved.

What is claimed is:
1. A method for manufacturing a magnesium fluoride sintered compact, the method comprising:

filling a magnesium fluoride powder material into a die by tapping; and performing pulsed electric current sintering for sintering the filled magnesium fluoride powder material while applying a pulsed electric current thereto, to obtain a magnesium fluoride sintered compact.

2. The method for manufacturing a magnesium fluoride sintered compact according to claim 1, wherein, in the powder filling, the magnesium fluoride powder material is a high-purity material having a purity of 99 percent by mass or higher, and the rest thereof contains inevitable impurities.

3. A method for manufacturing a neutron moderator, the method comprising:

preparing a plurality of disc-shaped magnesium fluoride sintered compacts manufactured by the method for manufacturing a magnesium fluoride sintered compact according to claim 1; and layering and joining the disc-shaped magnesium fluoride sintered compacts to manufacture a neutron moderator.

4. The method for manufacturing a neutron moderator according to claim 3, wherein in the layering and joining, when the disc-shaped magnesium fluoride sintered compacts are used as intermediate bodies, at least one second intermediate layered body is layered, the second intermediate layered body being obtained by further drilling the intermediate bodies.

5. The method for manufacturing a neutron moderator according to claim 4, wherein in the layering and joining, when the disc-shaped magnesium fluoride sintered compacts are used as intermediate bodies, at least one third intermediate layered body is layered, the third intermediate layered body being obtained by tapering an outer periphery of the intermediate bodies.

6. The method for manufacturing a neutron moderator according to claim 5, wherein in the layering and joining, a neutron moderator is manufactured by layering a first intermediate layered body in which the intermediate bodies are layered, the second intermediate layered body, and the third intermediate layered body.

7. A neutron moderator that moderates neutrons, the neutron moderator comprising an intermediate layered body in which a plurality of disc-shaped magnesium fluoride sintered compacts are layered.

* * * * *